(12) United States Patent
Kurihara et al.

(10) Patent No.: US 7,598,490 B2
(45) Date of Patent: Oct. 6, 2009

(54) SEM-TYPE REVIEWING APPARATUS AND A METHOD FOR REVIEWING DEFECTS USING THE SAME

(75) Inventors: Masaki Kurihara, Utsunomiya (JP); Toshifumi Honda, Yokohama (JP); Ryo Nakagaki, Kawasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 322 days.

(21) Appl. No.: 11/747,253

(22) Filed: May 11, 2007

(65) Prior Publication Data

US 2008/0067371 A1 Mar. 20, 2008

(30) Foreign Application Priority Data

May 11, 2006 (JP) .............................. 2006-132188

(51) Int. Cl.
- *G06K 9/00* (2006.01)
- *G01N 23/00* (2006.01)
- *G21K 7/00* (2006.01)
- *A61N 5/00* (2006.01)
- *G21G 5/00* (2006.01)

(52) U.S. Cl. ....................... 250/307; 250/306; 250/310; 250/311; 250/492.2; 382/145; 382/148; 382/149

(58) Field of Classification Search ................. 250/306, 250/307, 310, 311, 492.2; 382/145, 148, 382/149

See application file for complete search history.

(56) References Cited

U.S. PATENT DOCUMENTS

| | | | |
|---|---|---|---|
| 6,122,397 A * | 9/2000 | Lee et al. ..................... 382/149 |
| 7,155,052 B2 * | 12/2006 | Geshel et al. ............... 382/144 |
| 7,423,746 B2 * | 9/2008 | Takeda et al. ............... 250/306 |
| 7,425,704 B2 * | 9/2008 | Miyai et al. .................. 250/307 |
| 7,432,503 B2 * | 10/2008 | Honda et al. ................ 250/307 |
| 2002/0181757 A1 * | 12/2002 | Takeuchi ..................... 382/149 |
| 2004/0105578 A1 * | 6/2004 | Tsuchiya et al. ............ 382/144 |
| 2006/0193507 A1 * | 8/2006 | Sali et al. .................... 382/145 |

(Continued)

FOREIGN PATENT DOCUMENTS

JP 2000-030652 1/2000

(Continued)

*Primary Examiner*—Jack I Berman
*Assistant Examiner*—Brooke Purinton
(74) *Attorney, Agent, or Firm*—Antonelli, Terry, Stout & Kraus, LLP.

(57) ABSTRACT

In order to achieve high throughput in a SEM-type defect-reviewing apparatus and method for automatically acquiring images of review defects present on samples, including: a cell comparison step subdivided into the steps of (a) providing a defect detection success ratio or defect detection success map due to at least a cell comparison scheme for each wafer or each chip, (b) selecting a review sequence of either the cell comparison scheme or a die comparison scheme on the basis of the provided defect detection success ratio or defect detection success map, (c) if the cell comparison scheme is selected, judging whether detection of the review defect is possible by executing the cell comparison scheme; and a die comparison step in which die comparison is performed if the judgment result indicates that the detection of the review defect is impossible, or if the die comparison scheme is selected in the selection step.

21 Claims, 12 Drawing Sheets

U.S. PATENT DOCUMENTS

2006/0280358 A1 * 12/2006 Ishikawa .................... 382/149

FOREIGN PATENT DOCUMENTS

| JP | 2000-067243 | 3/2000 |
| JP | 2001-331784 | 11/2001 |
| JP | 2002-310962 | 10/2002 |
| JP | 2002-323458 | 11/2002 |
| JP | 2003-098114 | 4/2003 |

* cited by examiner

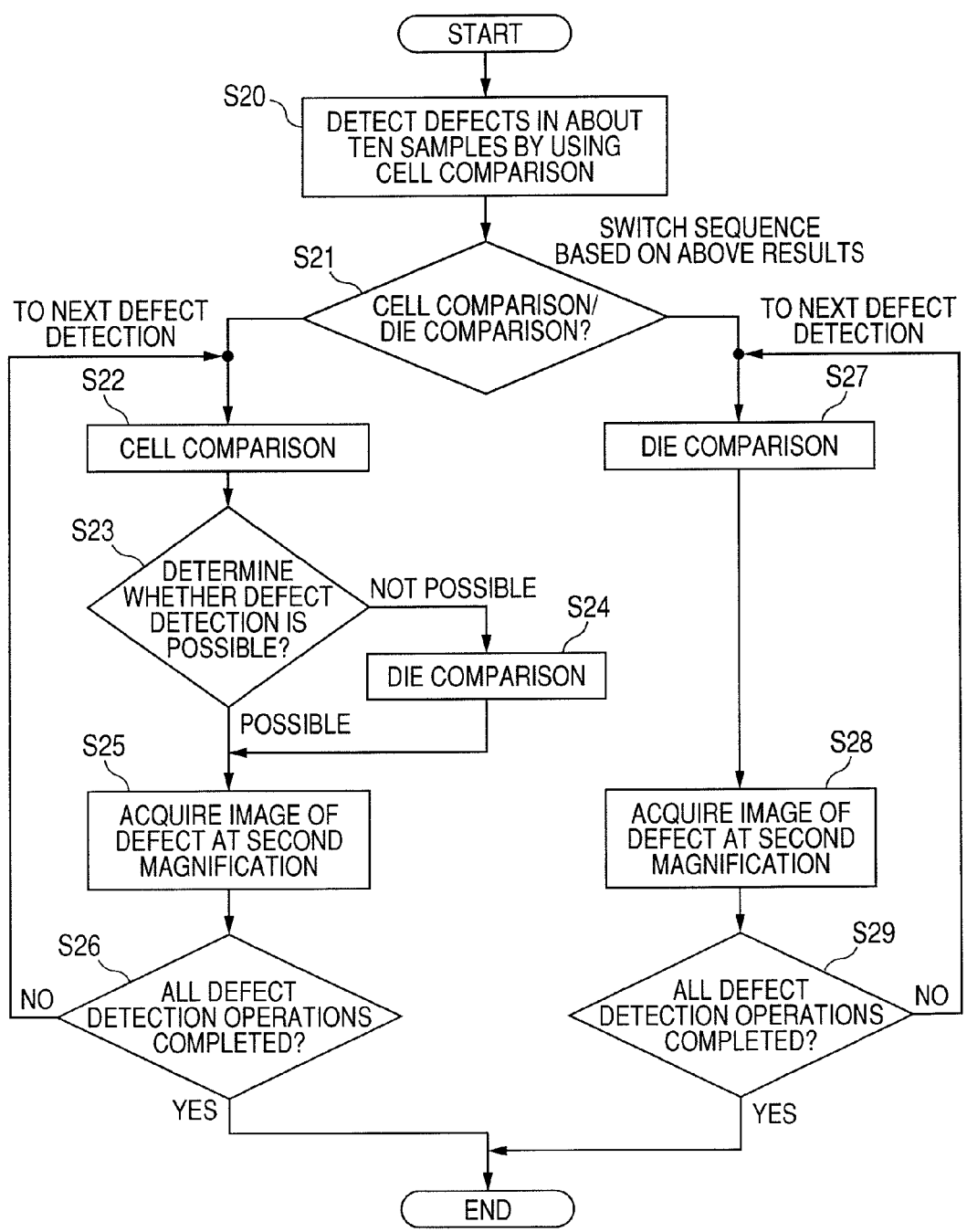

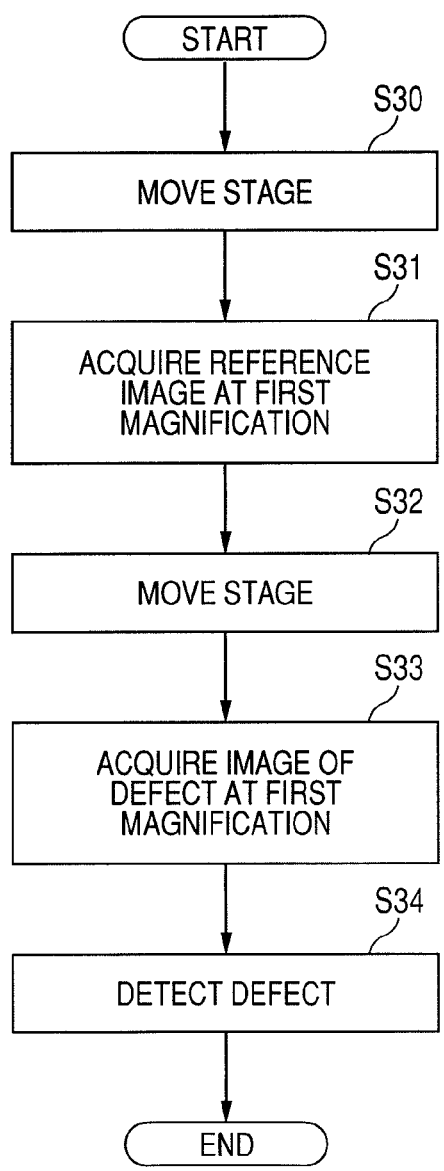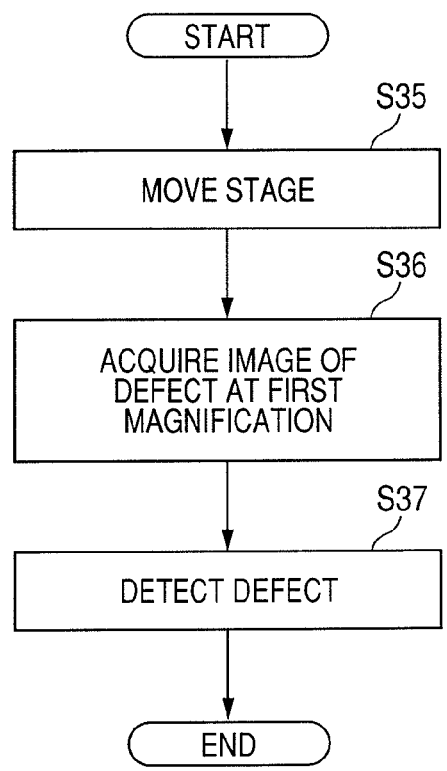
FIG. 3A
FIG. 3B

SEM-TYPE REVIEWING APPARATUS AND A METHOD FOR REVIEWING DEFECTS USING THE SAME

BACKGROUND OF THE INVENTION

The present invention relates to a SEM-type defect-reviewing apparatus that uses a detection system of a scanning electron microscope (SEM) to automatically acquire high-resolution images of any semiconductor wafer surface defects detected by an inspection apparatus during manufacturing processes for semiconductor products. The invention also relates to a method for reviewing defects using the SEM-type defect-reviewing apparatus.

To achieve early ramp-up of high yield manufacturing of large-scale integrated circuits and stable operation of their manufacturing process equipment, information on the occurrence of the defects detected by visual inspection apparatus, must be analyzed rapidly and utilized for defect route cause analysis. Reviewing apparatuses that automatically acquire high-resolution images of the inspection apparatus-detected defects in order to analyze obtained defect information are broadly divided into a type having an optical detection system, and a type having a detection system based on a scanning electron microscope (SEM). Compared with the optical type of reviewing apparatus, the SEM type of reviewing apparatus can obtain detailed defect images. For this reason, adoption of the SEM type of reviewing apparatus capable of obtaining high-resolution images is increasing with finer wiring patterns on semiconductor wafers. However, since SEM images require a longer acquisition time than optical images, the SEM type of reviewing apparatus has the problem that its throughput (hourly defect detection capability) is low, compared with that of the optical type of reviewing apparatus.

Known conventional techniques relating to such a SEM-type reviewing apparatus are disclosed in JP-A Nos. 2002-310962 (Patent Document 1), 2000-67243 (Patent Document 2), 2003-98114 (Patent Document 3), 2000-30652 (Patent Document 4), and 2002-323458 (Patent Document 5).

JP-A-2002-310962 describes an image acquisition apparatus that uses a SEM to automatically form and acquire images of any plural surface defect sections of a semiconductor wafer. This image acquisition apparatus has a scheduling unit for determining a defect-imaging sequence and a moving speed of a stage from a positional relationship between the defective sections on the wafer, and a control unit for feeding back to the quantity of beam deflection a moving distance of the stage. The scheduling unit and the control unit make it possible to form and acquire the images of the plural defective sections while moving the stage along an ideal route.

Also, JP-A-2000-67243 describes an automatic defect information acquisition method that uses a SEM. In this defect information acquisition method, a user can efficiently detect defects by assigning pattern information on an object to be inspected, since there is no need, for example, to move a field of view of the SEM to a reference point when inspecting a non-patterned or cyclically patterned region.

JP-A-2003-98114 describes a method for inspecting and reviewing defects using a SEM. This method includes splitting a defect image into regions of a grid format, then executing pattern matching (or the like) to evaluate whether a split image region to be inspected is similar to other split image regions, and if the evaluated region has no similarity to any other regions, identifying defect positions in that region because of the defects being regarded as included therein.

JP-A-2000-30652 describes a method for reviewing a sample using a SEM. In this reviewing method, information on defects which have been detected on the sample by an inspection apparatus is first used to image the sample and obtain a reference image not including the detected defects. Next after the information relating to the detected defects has been used to image the sample and obtain a defect image including the detected defects, the reference image and the defect image are compared and the defects within the defect image are detected. Additionally, an enlarged image of the detected defects is obtained by imaging part of a region in which the detected defects have been imaged above, then a background region is erased from the enlarged image, and the resulting image without the background region is displayed.

JP-A-2002-323458 describes a SEM-type apparatus for reviewing defects. In this apparatus, during acquisition of approximate defect position coordinates obtained during inspection with an inspection apparatus, whether the defect occurred in a cell section, a non-cell section, a section with dense patterns, or other sections, is first judged using layout data. Next, an image detection mode (a mode for determining whether a reference image is to be detected) and inspection parameters including an imaging magnification are set up according to particular judgment results, and management standards relating to criticality are established.

As outlined above, a cell comparison scheme and a die comparison scheme are used as the methods of acquiring defect images based on SEM images. The cell comparison scheme, compared with the die comparison scheme, is high in throughput, but is limited in the number of applicable semiconductor wafer types, whereas the die comparison scheme, compared with the cell comparison scheme, is low in throughput, but is applicable to almost all types of semiconductor wafers. Regions to which the cell comparison scheme can be applied, and regions to which the cell comparison cannot be applied are usually present in mixed form in a semiconductor wafer region to be reviewed, so it is difficult to improve throughput by adopting only the cell comparison scheme. To perform defect detection operations and detailed analyses while maintaining optimal throughput for semiconductor wafers, therefore, both the cell comparison scheme and die comparison scheme that are review sequences must be selected for each semiconductor wafer inspected or for each defect inspected.

However, none of the above five Patent Documents (1 to 5) has paid sufficient consideration to the fact that a review sequence suited to each semiconductor wafer and defect to be analyzed can be automatically selected using defect detection results obtained at least in the cell comparison scheme.

SUMMARY OF THE INVENTION

The present invention provides a SEM-type defect-reviewing apparatus constructed so that a review sequence suited to each of semiconductor wafers and defects to be analyzed can be automatically selected using defect detection results, and thus so that optimal throughput relating to detailed analysis of the defects reviewed can be maintained for various semiconductor wafers. The invention also provides a method for reviewing defects using the above apparatus.

That is to say, an aspect of the present invention relates to a method for reviewing defects using a SEM-type reviewing apparatus, in which, after position coordinate data of review defects on wafer has been obtained from an inspection apparatus, a stage with wafer mounted thereon is moved in accordance with the position coordinate of the review defect and then an electron beam defect image of each review defect is acquired by imaging at a low magnification using an electron beam optical system.

The above method includes: a cell comparison step subdivided into four major steps of (a) acquiring an electron beam defect image of a low magnification by moving a stage on which the wafer is mounted in accordance with position coordinate of a review defect on the wafer obtained from an inspection apparatus, and then imaging the review defect at the low magnification by using an electron beam optical system, (b) selecting a review sequence of either a cell comparison scheme or a die comparison scheme on the basis of a defect detection success ratio or defect detection success map due to at least the cell comparison scheme for each wafer or for each chip formed on the wafer, (c) if the cell comparison scheme is selected in the sequence selection step, judging whether detection of the review defect is possible (successful) by executing the selected cell comparison scheme based on the electron beam defect image acquired from the review defect at the low magnification, and (d) a first calculation step of, if judgment result in the detection possibility judgment step indicate that the detection of the review defect is possible (successful), calculating position coordinate of the detected review defect in a coordinate system of a defect-reviewing apparatus; a die comparison step subdivided into two major steps of (a) if the judgment result in the detection possibility judgment step indicates that the detection of the review defect is impossible (unsuccessful), or if the die comparison scheme is selected in the sequence selection step, acquiring an electron beam reference image of a low magnification of a normal part to perform the selected die comparison scheme by using the electron beam optical system with moving the stage, and (b) a second calculation step of detecting the review defect by performing the selected die comparison scheme between the acquired electron beam defect image of the review defect at the low magnification and the acquired electron beam reference image of the low magnification, and calculating the position coordinate of the detected review defect in the coordinate system of the defect-reviewing apparatus; and a defect image acquisition step of acquiring an electron beam defect images of a high magnification by imaging the review defect at the high magnification by using of the electron beam optical system in accordance with the position coordinates of the review defects calculated in the coordinate system of the defect-reviewing apparatus in the first and second calculation steps.

Another aspect of the present invention relates to a method for reviewing defects using a SEM-type reviewing apparatus, in which, after position coordinate data of review defects on wafer has been obtained from an inspection apparatus, a stage with wafer mounted thereon is moved in accordance with the position coordinate of the review defect and then an electron beam defect image of each review defect is acquired by imaging at a low magnification using an electron beam optical system.

The above method includes: a cell comparison step subdivided into five major steps of (a) acquiring an electron beam defect image of a low magnification by moving a stage on which the wafer is mounted in accordance with position coordinate of a review defect on the wafer obtained from an inspection apparatus, and then imaging the review defect at the low magnification by using an electron beam optical system, (b) previously providing (preparing) a defect detection success ratio or defect detection success map due to at least the cell comparison scheme for each wafer or for each chip formed on the wafer, (c) selecting a review sequence of either a cell comparison scheme or a die comparison scheme on the basis of the provided (prepared) defect detection success ratio or defect detection success map due to at least the cell comparison scheme for each wafer or for each chip formed on the wafer, (d) if the cell comparison scheme is selected in the sequence selection step, judging whether detection of the review defect is possible (successful) by executing the cell comparison scheme based on the electron beam defect image acquired from the review defect at the low magnification, and (e) a first calculation step of, if judgment result in the detection possibility judgment step indicates that the detection of the review defect is possible (successful), calculating position coordinate of the detected review defect in a coordinate system of a defect-reviewing apparatus; a die comparison step subdivided into two major steps of (a) if the judgment result in the detection possibility judgment step indicates that the detection of the review defect is impossible (unsuccessful), or if the die comparison scheme is selected in the sequence selection step, acquiring an electron beam reference image at a low magnification for a normal part to perform the die comparison scheme by using the electron beam optical system with moving the stage, and (b) a second calculation step of detecting the review defect by performing the die comparison scheme between the acquired electron beam defect image of the review defect at the low magnification and the acquired electron beam reference image of the low magnification, and calculating the position coordinate of the detected review defect in the coordinate system of the defect-reviewing apparatus; and a defect image acquisition step of acquiring an electron beam defect images of a high magnification by imaging the review defects at the high magnification by using the electron beam optical system in accordance with the defect position coordinates calculated in the coordinate system of the defect-reviewing apparatus in the first and second calculation steps.

According to the present invention, in a SEM-type defect-reviewing apparatus, a review sequence suited to each semiconductor wafer and each defect to be analyzed can be automatically selected on the basis of detection results on defects to be reviewed, and thus, optimal throughput relating to detailed analysis of the defects reviewed can be maintained for various semiconductor wafers.

These and other objects, features, and advantages of the invention will be apparent from the following more particular description of preferred embodiments of the invention, as illustrated in the accompanying drawings.

BRIEF DESCRIPTION OF THE DRAWINGS

FIG. 2 is a flowchart showing a first embodiment of a review sequence adapted for detailed analysis of defects in the SEM-type defect-reviewing apparatus of the present invention;

FIGS. 3A and 3B are flowcharts of review sequences according to the present invention, FIG. 3A being a flowchart showing an example of a review sequence based on a die comparison scheme according to the invention, and FIG. 3B being a flowchart showing an example of a review sequence based on a cell comparison scheme according to the invention;

DETAILED DESCRIPTION OF THE PREFERRED EMBODIMENTS

Embodiments of the present invention relating to an apparatus and method for reviewing defects using a SEM (Scanning Electron Microscope) will be described hereunder using the accompanying drawings.

First Embodiment

Figure 1:
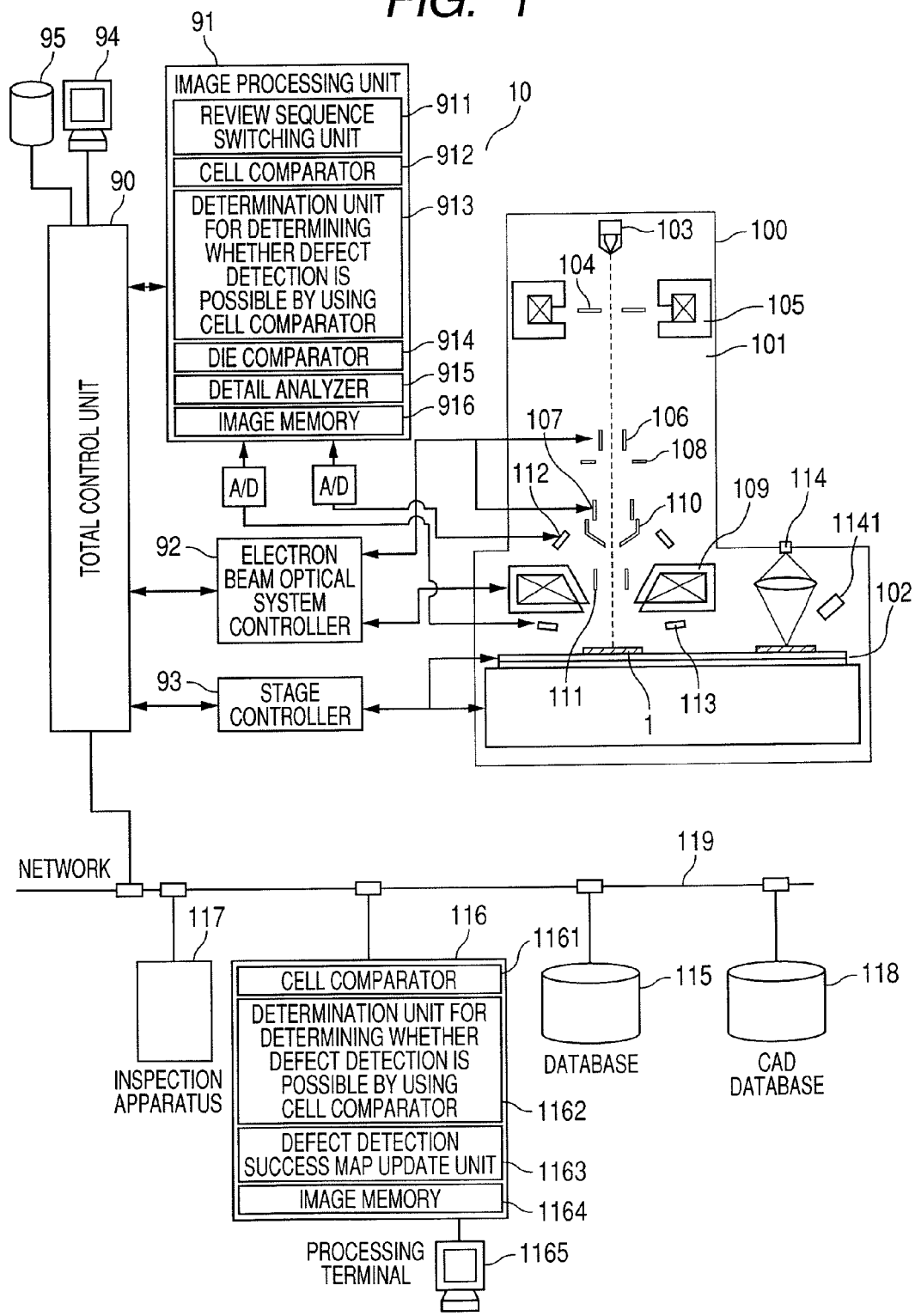
FIG. 1 is a schematic configuration diagram showing an embodiment of a semiconductor SEM-type defect-reviewing apparatus according to the present invention.

A first embodiment of a SEM-type defect-reviewing apparatus according to the present invention is described below using FIG. 1. FIG. 1 is a configuration diagram showing the first embodiment of a SEM-type defect-reviewing apparatus for conducting detailed analyses on semiconductor wafer surface defects according to the present invention. The SEM-type defect-reviewing apparatus 10 includes a vacuum chamber 100, a total control unit 90, an image processing unit 91, an electron beam optical system controller 92, and a stage controller 93. The vacuum chamber 100 includes an XY stage 102 for moving a wafer 1, an electron beam optical system 101 for irradiating the wafer 1 with electron beams, and an optical microscope unit 114 with an illumination optical system 1141 for bare wafer defect detection. The electron beam optical system 101 includes an electron gun 103. The electron beam optical system 101 also includes, as its electron beam control elements, electron beam extraction electrodes 104, condenser lenses 105, blanking deflectors 106, scanning deflectors 107, aperture stops 108, objective lenses 109, reflectors 110, and ExB deflectors 111. In addition, the electron beam optical system 101 includes a secondary electron detector 112 and/or backscattered electron detectors 113, the secondary electron detector 112 and/or backscattered electron detectors 113 being constructed to respectively detect secondary electrons and/or backscattered electrons stemming from the wafer 1.

The total control unit 90 controls the entire defect-reviewing apparatus by having the image processing unit 91, the electron beam optical system controller 92, and the stage controller 93 each connected to the total control unit 90. A display device 94 with a graphical user interface (GUI) function block having an input/output tool, and a storage device 95 are also connected to the total control unit 90. The total control unit 90 transmits/receives parameters and instructions to the electron beam optical system controller 92, the stage controller 93, and the image processing unit 91. The total control unit 90 is constructed so that various parameters can be set up arbitrarily or selectively according to particular needs. These parameters include: an accelerating voltage, electron beam deflection width (this determines an imaging magnification), and other parameters to specified to the electron beam optical system 101 via the electron beam optical system controller 92 prior to generation of the electron beams; timing and other parameters relating to signal acquisition from the secondary electron detector 112 and/or the backscattered electron detectors 113; and a moving speed of the XY stage 102 and other parameters that can be sent via the stage controller 93. A correction control circuit (not shown) that is provided in the total control unit 90 monitors wafer position and wafer height errors in accordance with signals from a position-monitoring critical-dimension measuring instrument (not shown) and wafer height measuring instrument (not shown) installed at the XY stage 102. The correction control circuit also makes a correction signal from obtained monitoring results and sends the made correction signal to an objective lens power supply (not shown) and scanning deflector signal generator (not shown) provided in the electron beam optical system controller 92 so that the irradiated electron beams always arrive at a correct position.

The secondary electrons and/or backscattered electrons that have been detected by the secondary electron detector 112 and/or the backscattered electron detectors 113 are input to a scintillator, in which the electrons are then converted into electrical signals. The electrical signals are further A-D converted to form electron beam images, which are then input to the image processing unit 91. The image processing unit 91 performs a defect detection process based on an electron beam image imaged at a first magnification (for example, 5,000 through 30,000 magnifications) and a defect detail analytical process based on an electron beam image formed at a second magnification (for example, 30,000 through 200,000 magnifications) higher than the first magnification. The image processing unit 91 includes a CPU and an image memory 916. The CPU is functionally divided into a review sequence switching (selecting) unit 911, a cell comparator 912, a determining unit 913 for determining whether the defect can be detected using the cell comparator, a die comparator 914, and a detail analyzer 915. That is to say, the review sequence switching (selecting) unit 911, the cell comparator 912, the determining unit 913 for determining whether the defect can be detected using the cell comparator, the die comparator 914, and the detail analyzer 915 may be constructed so that each is executed by software processing based on a program.

The detail analyzer 915 calculates electron beam image feature quantities of the defects to be reviewed, that is, shapes, brightness (grayscale levels), texture, and other factors, from associated defect position information in a coordinate system of the defect-reviewing apparatus, the defect position information being stored within the image memory 916, and from the electron beam defect image formed above at the second magnification. Next, the detail analyzer 915 acquires detailed analytical information (category information and classification information of the defects) from the electron beam image feature quantities (values), and stores the detailed analytical information as electron beam defect review results for each semiconductor wafer into a database 115.

Figure 7:
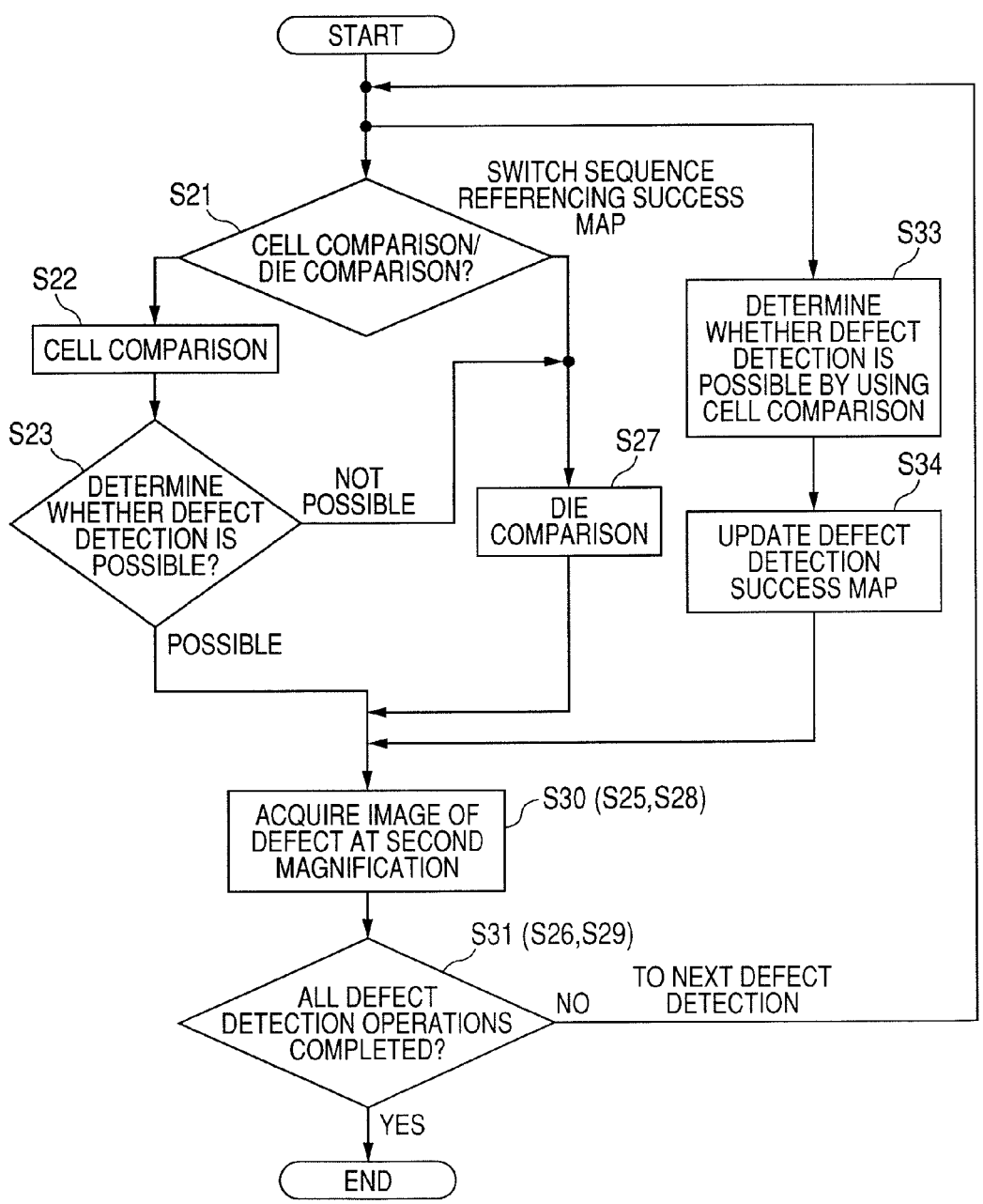
FIG. 7 is a flowchart showing a third embodiment of a review sequence adapted for detailed analysis of defects in the SEM-type defect-reviewing apparatus of the present invention.
Figure 11:
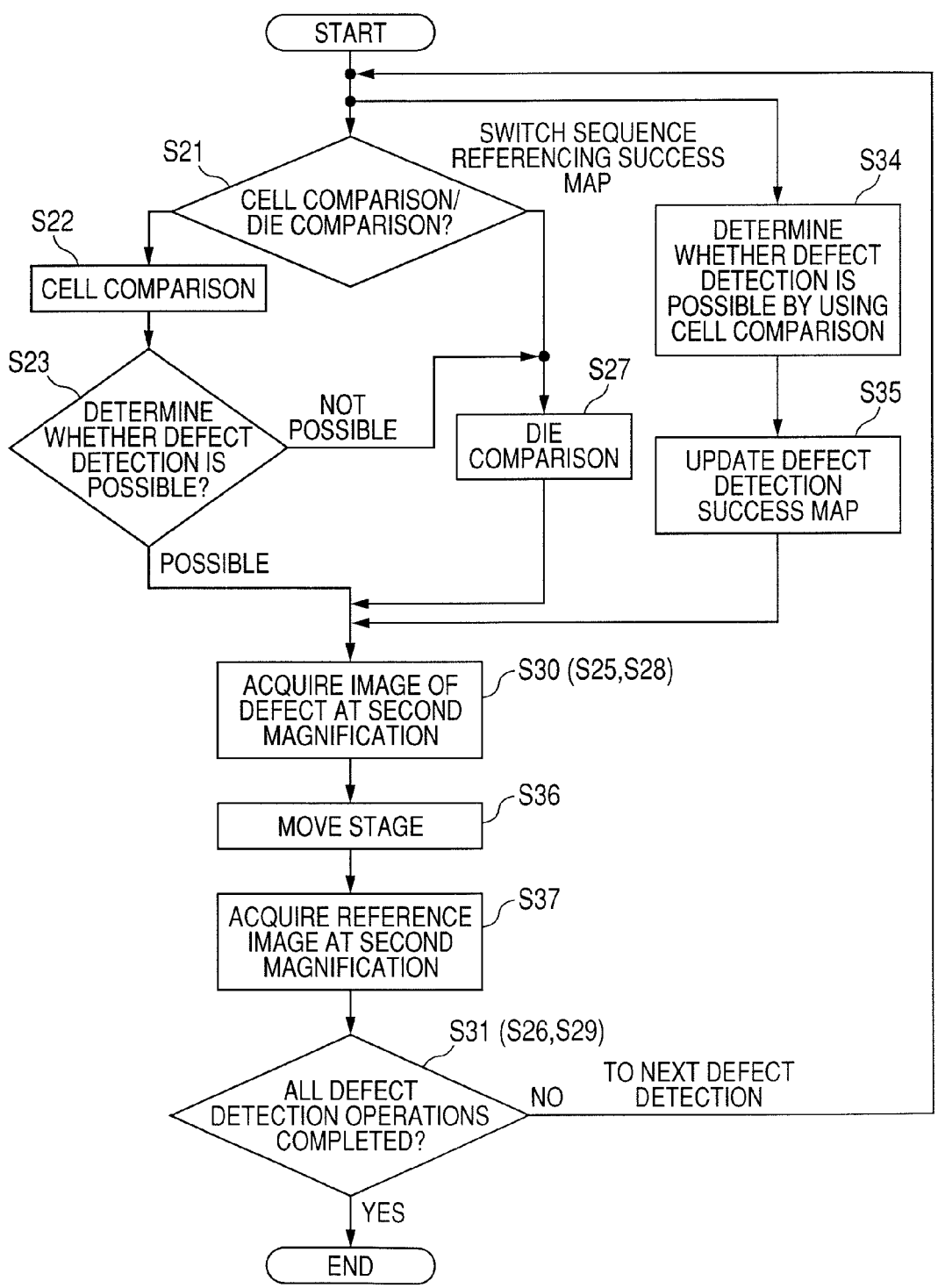
FIG. 11 is a flowchart showing a fourth embodiment of a review sequence adapted for detailed analysis of defects in the SEM-type defect-reviewing apparatus of the present invention.

The electron beam images that the SEM-type defect-reviewing apparatus 10 has formed using electron beams (i.e., the electron beam defect image in the cell comparison scheme, the electron beam reference image and electron beam reference image in the die comparison scheme, and the electron beam defect image formed at the second magnification for detailed analysis) are sent to the database 115 connected to the defect-reviewing apparatus 10 via a network 119 and saved together with information that specifies defect-reviewing apparatus operating parameters and the like. The results of processing by the image processing unit 91 (i.e., defect detection success ratios or defect detection success maps in the cell comparison scheme for each kind of semiconductor wafer and/or for each region on the semiconductor wafer, the defect position information in the coordinate system of the defect-reviewing apparatus, and electron beam image feature quantities (values) of the defects, such as shapes, brightness or grayscale levels, and texture) are also saved in the database 115 via the route described above. The same further applies to the detailed analytical information based on the electron beam image feature quantities (i.e., category information and classification information of the defects). Of course, defect inspection data (approximate defect position coordinate data) obtained in an inspection apparatus 117 may be appended to semiconductor wafer classification information before being stored into the database 115. A processing terminal 116, the inspection apparatus 117, and a CAD database 118 that contains layout data which is information on wiring patterns formed on the semiconductor wafer are also connected to the network 119, and access can be made to the images, defect information, and semiconductor wafer information existing within the database 115 (the semiconductor wafer information includes the information relating to the kind of semiconductor wafer, and the layout information that is design information of the wafer). The processing terminal 116 includes the CPU that can conduct parallel processing with the image processing unit 91 (the CPU is functionally divided into a cell comparator 1161, a judgment unit 1162 for judging whether the review defect can be detected by using the cell comparator, a defect detection success map update unit 1163, and an image memory 1164 or the like; the cell comparator 1161, the judgment unit 1162 for judging whether the review defect can be detected by using the cell comparator, and the defect detection success map update unit 1163 may be constructed so that each is executed by software processing based on a program). That is to say, the processing terminal 116 is constructed so that concurrently with the defect detection process for defect reviews by the image processing unit 91 of the defect-reviewing apparatus 10, the terminal 116 can conduct a process which, as shown in FIGS. 7 and 11, includes the step (S30) of determining whether the defect to be reviewed can be detected using the cell comparator, and the step (S31) of updating a defect detection success map based on results of the above determination.

Next, defect detection and defect detail analysis sequences in the first embodiment of the present invention are described below using FIG. 2. That is to say, the invention improves throughput by, in the defect detection sequence, maximizing the number of defects to be reviewed using the cell comparison scheme according to the invention, and minimizing the number of defects to be reviewed using the die comparison scheme according to the invention. The cell comparison scheme according to the invention uses, for example, a method of creating an electron beam reference image beforehand by means of electron beam imaging of an repeating pattern (cell section), or a method of creating an electron beam reference image by combining an electron beam defect image that has been acquired beforehand by electron beam imaging at a first magnification, and an image obtained from erasing the defect from the electron beam defect image. In the cell comparison scheme of the invention, therefore, throughput can be improved over that achievable in the die comparison scheme of the invention, since the stage movement intended to form an electron beam reference image can be made unnecessary by omitting the electron beam reference imaging operation in the die comparison scheme.

For defect reviews, various kinds of semiconductor wafers that were inspected by the inspection apparatus 117 are loaded onto the XY stage 102 of the SEM-type defect-reviewing apparatus 10 according to the present invention.

According to the first embodiment of the present invention, therefore, in step S20, among all defects having defect inspection data (approximate position coordinate data of the defect), only several (say, about 10) defects are specified as samples for each semiconductor wafer that was inspected by the inspection apparatus 117, and the defect samples to be reviewed are detected in the cell comparison scheme which makes throughput improvable. Next in step S21, whether the defects are to be further inspected in the cell comparison scheme or the die comparison scheme is selected according to a particular success ratio of the defect detection in the cell comparison scheme (i.e., whether the acquisition of an electron beam reference image at a low magnification, namely, a first magnification, is to be executed for each wafer) [if yes, the die comparison scheme is to be adopted; if no, the cell comparison scheme is to be adopted]. If the success ratio of the defect detection in the cell comparison scheme is higher than a required reference value, the defects to be reviewed are detected in step S22 using the cell comparison scheme that is high in throughput. If the success ratio of the defect detection in the cell comparison scheme is lower than the required reference value, the defects to be reviewed are detected in step S27 using the die comparison scheme. In this manner, throughput in the defect detection of one entire set of defects to be reviewed can be improved.

That is to say, in the present first embodiment, for each semiconductor wafer or each set of wafers to be reviewed, several (say, about 10) of all inspected defects are detected as samples in the cell comparison scheme in step S20. Next, it is determined in step S21 whether, based on detection of the sample defect, the review sequence for each semiconductor wafer is to be executed in the die comparison scheme or the cell comparison scheme (i.e., whether the acquisition of an electron beam reference image at the low magnification, namely, the first magnification, is to be executed for each wafer). This method is applied for the following reason. That is, for a memory product, most of the wiring patterns formed on the wafer are repeating patterns, whereas, for a logic product, most of the wiring patterns formed on the semiconductor wafer are non-repeating patterns, so whether the defects on the semiconductor wafer can be detected using the cell comparison scheme is usually determinable just by detecting the several defect samples. For this reason, for a memory product, defects present in the memory cell section occupying a large portion of the semiconductor wafer's effective surface area can be detected using the cell comparison scheme. In this case, since the logic section occupying only a small portion of the effective surface area cannot be subjected to the defect detection in the cell comparison scheme, defects present in this region need to be detected using the die comparison scheme. At this time, switching from the cell comparison scheme to the die comparison scheme makes it necessary to move the stage once too often than in normal die comparison scheme. However, for example, when the defect detection process is conducted for 500 defect samples, if the moving speed of the stage is 500 milliseconds, the electron beam image acquisition time required is 300 milliseconds, and an auto-focusing time is 200 milliseconds, provided that a minimum of about 200 samples can be detected in the cell comparison scheme, throughput in the present first embodiment can be improved over the throughput obtainable by using only the die comparison scheme.

Another feature of the first embodiment according to the present invention is described below. Selection of the cell comparison scheme in step S11 for each semiconductor wafer in the review sequence that was determined in step S21 according as the memory cell section occupies a large majority of the effective area does not mean that all of the defects on the semiconductor wafer 1 to be reviewed can be detected in the cell comparison scheme. Therefore, for each subsequent defect or for each subsequent set of defects, it is first determined in step S23 whether the defect can be detected in the cell comparison scheme. If results of the determination indicate that the defect can be detected, a detection signal of the defect is output, or if the determination results indicate that the defect cannot be detected, step S24 is executed to select the die comparison scheme reliable in the defect detection (the use of the die comparison scheme, however, requires the acquisition of an electron beam reference image at the first magnification) and detect the defect. After this, the defect that has thus been detected for a review is imaged at a second magnification by electron beam irradiation in step S25. Next, step 26 is executed to repeat the above procedure for all other defects on the wafer that are to be reviewed. It is thus possible to detect all review target defects on each semiconductor wafer, and to acquire electron beam defect images whose electron beam image feature values (shapes, brightness or grayscale levels, texture, and other factors) can be calculated for detailed analysis.

In addition to, in review sequence of the step S21 determined in each semiconductor wafer, when switching to the die comparison scheme of the step S27, the defect is detected with the die comparison scheme for review defect on the semiconductor wafer 1 and the detected review defect is imaged at the second magnification with the electron beam in the step S28. After this, step 29 is executed to repeat the above procedure for all other review defects. It is thus possible to detect all review defects on each semiconductor wafer, and to acquire electron beam defect images whose electron beam image feature quantities can be calculated for detailed analysis.

Next, the above is described in further detail below. Suppose that the defects to be reviewed are already inspected in the coordinate system of the inspection apparatus 117 and that the approximate position coordinates of these defects are already stored within the image database 115. In a normal ADR (Automatic Defect Review) sequence, the semiconductor wafer 1 to be reviewed and analyzed is mounted on the XY stage 102 of the defect-reviewing apparatus 10, and inspection data that is the results of the inspection with the inspection apparatus 117 is read in from the image database 115, for example, and stored into the storage device 95, for example. Next, the defect data of the semiconductor wafer 1 that has been stored into the storage device 95, for example, is displayed on the GUI screen of the display device 94, and several (say, about 10) of the defects to be reviewed are specified as samples by use of the input tool 94. The defect-reviewing apparatus 10 then executes step S20 to detect all specified (say, about 10) defect samples by conducting cell comparative inspections with the cell comparator 912 or the like. After the detection of the semiconductor wafer defect samples (say, about 10 pieces) by the cell comparator 912 or the like, the review sequence switching (selecting) unit 911 operates appropriately according to the particular detection results (information on whether the defects have been successfully detected). If the ratio of the successfully detected defect samples to all specified defect samples (i.e., the success ratio of the defect detection) is equal to or greater than the required reference value (say, about 40% to 50%), that is, in this example, if defects have been actually detected on at least about four to five of the defect samples, subsequent defect detection also uses the cell comparison scheme expected to improve throughput. If the above defect detection success ratio is less than about 40% to 50%, the review sequence is switched in step S21 so that the subsequent defect detection uses the die comparison scheme more reliable in terms of defect detection. A reference value (threshold value) for determining whether the use of the review sequence is to be continued is uniquely determined by a processing time required of the die comparison scheme in step S27, and a processing time required of the cell comparison scheme in step S22 (this processing time includes the time required for switching to the die comparison scheme in the event of a defect detection failure). For example, as described above in the first embodiment, if the moving speed of the stage is 500 milliseconds, the electron beam image acquisition time required is 300 milliseconds, and the auto-focusing time is 200 milliseconds, provided that a minimum of about 40% of all defects to be reviewed can be detected in the cell comparison scheme, the cell comparison scheme improves in throughput, compared with the die comparison scheme.

Next, if the success ratio of the defect detection by cell comparisons based on the several defect samples to be reviewed is high and the cell comparison scheme expected to improve throughput is selected for each semiconductor wafer (or for each set of wafers) in step S22 by the review sequence switching unit 911, step S23 is executed for the cell comparator 912 or the like to conduct a cell comparative inspection on each subsequent defect to be reviewed, and for the defect detection possibility judgment unit 913 to determine whether the defect can be successfully detected during the cell comparative inspection. If determination results indicate that the detection is impossible, a die comparison inspection high in defect detection reliability, compared with the cell comparative inspection, is conducted in step S24 by the die comparator 914 or the like. Next, the defect-reviewing apparatus 10 executes step S25 to image the defect at the defect position in the coordinate system of the reviewing apparatus 10, at a second magnification higher than the first magnification, and stores the defect image together with the defect position information into the image memory 916, for example. Whether all necessary defects have been analyzed is confirmed in step S26. If there are any defects still remaining unanalyzed for reviews, processing is switched to next defect to be reviewed. If all defects have been analyzed, the analytical process is completed.

Next, if the success ratio of the defect detection by the cell comparisons based on the several defect samples to be reviewed is low and the die comparison scheme is selected for each semiconductor wafer (or for each set of wafers) in step S27 by the review sequence switching unit 911, the die comparator 914 or the like detects all defects on the semiconductor wafer by conducting die comparative inspections higher in defect detection reliability. Next, the defect-reviewing apparatus 10 executes step S28 to image the defect at the defect position in the coordinate system of the reviewing apparatus 10, at the second magnification higher than the first magnification, and stores the defect image together with the defect position information into the image memory 916, for example. Whether all necessary defects have been analyzed is confirmed in step S29. If there are any defects still remaining unanalyzed for reviews, processing is switched to next defect to be reviewed. If all defects have been analyzed, the analytical process is completed.

As described above, the cell comparison/die comparison review sequence based on the success ratio of the defect detection using the cell comparison scheme suitable for the repeating patterns for the several defect samples that are to be reviewed is selected for each semiconductor wafer (or for each set of wafers) in step S21. When the die comparison scheme is selected, all defects on the semiconductor wafer are detected in steps S27-S29 using the die comparison scheme higher in defect detection reliability. When the cell comparison scheme expected to improve throughput is selected, step S23 is executed to determine whether the defects can each be detected using the cell comparison scheme. If results of the determination indicate that the defect can successfully be detected, the defect detection in the cell comparison scheme is continued for each subsequent defect. If the determination results indicate that the defect cannot successfully be detected, the die comparison scheme is adopted to conduct defect inspections in step S24. The detection of all defects on the semiconductor wafer to be reviewed is thus improved in throughput.

Next, the die comparison scheme and cell comparison scheme that are the methods of identifying the positions of defects in the coordinate system of the defect-reviewing apparatus according to the present invention are described below using FIG. 3. In the die comparison scheme executed by the die comparator 914 (or the like) according to the present invention, as flowcharted in FIG. 3A, the total control unit 90 reads out, from the CAD database 118, die layout information that is the design information of the semiconductor wafer mounted on the XY stage 102, then stores the die layout information into the storage device 95, for example, and in accordance with information such as the stored die layout information and the approximate defect position coordinate information obtained as inspection results in the inspection apparatus 117, controls the stage 102 via the stage controller 93 in order to move the stage to a nondefective (normal) section on an adjacent die present on the wafer. These operations including the control of the stage are conducted in step S30. In next step S31, the total control unit 90 controls the electron beam optical system controller 92, acquires an electron beam reference image by imaging the nondefective (normal) section at a first magnification, and stores the image into the image memory 916, for example. In step S32, the total control unit 90 controls the stage 102 via the stage controller 93 in accordance with information such as the approximate defect position coordinate information obtained as inspection results in the inspection apparatus 117, then after moving the stage from the above-mentioned adjacent die to a desired defect position on a defective die, acquires an electron beam defect image by controlling the electron beam optical system controller 92 and imaging the defect at the first magnification by using electron beam imaging, and stores the image into the image memory 916, for example. After this, in step S34, the die comparator 914 (or the like) of the image processing unit 91 detects the associated die by comparing the above-mentioned electron beam reference image obtained from the nondefective adjacent die and stored within the image memory 916, for example, and the above-mentioned electron beam defect image obtained from the defective die, recalculates the position of the detected defect in the coordinate system of the reviewing apparatus, associates the thus-recalculated data with at least the electron beam defect image, stores the data into the image memory 916, for example.

As described above, since a plurality of dies each formed with the same wiring pattern thereon are arrayed on the semiconductor wafer, nondefective dies adjacent to defective ones are present. For this reason, an electronic beam reference image associated with an electron beam defect image can always be acquired and the defects to be reviewed can be reliably detected by die comparisons. For the die comparisons, however, the acquisition of an electron beam reference image and an electron beam defect image must be repeated for all intended defects by moving the stage. The die comparison scheme, therefore, decreases in throughput, compared with the cell comparison scheme.

Figure 12:
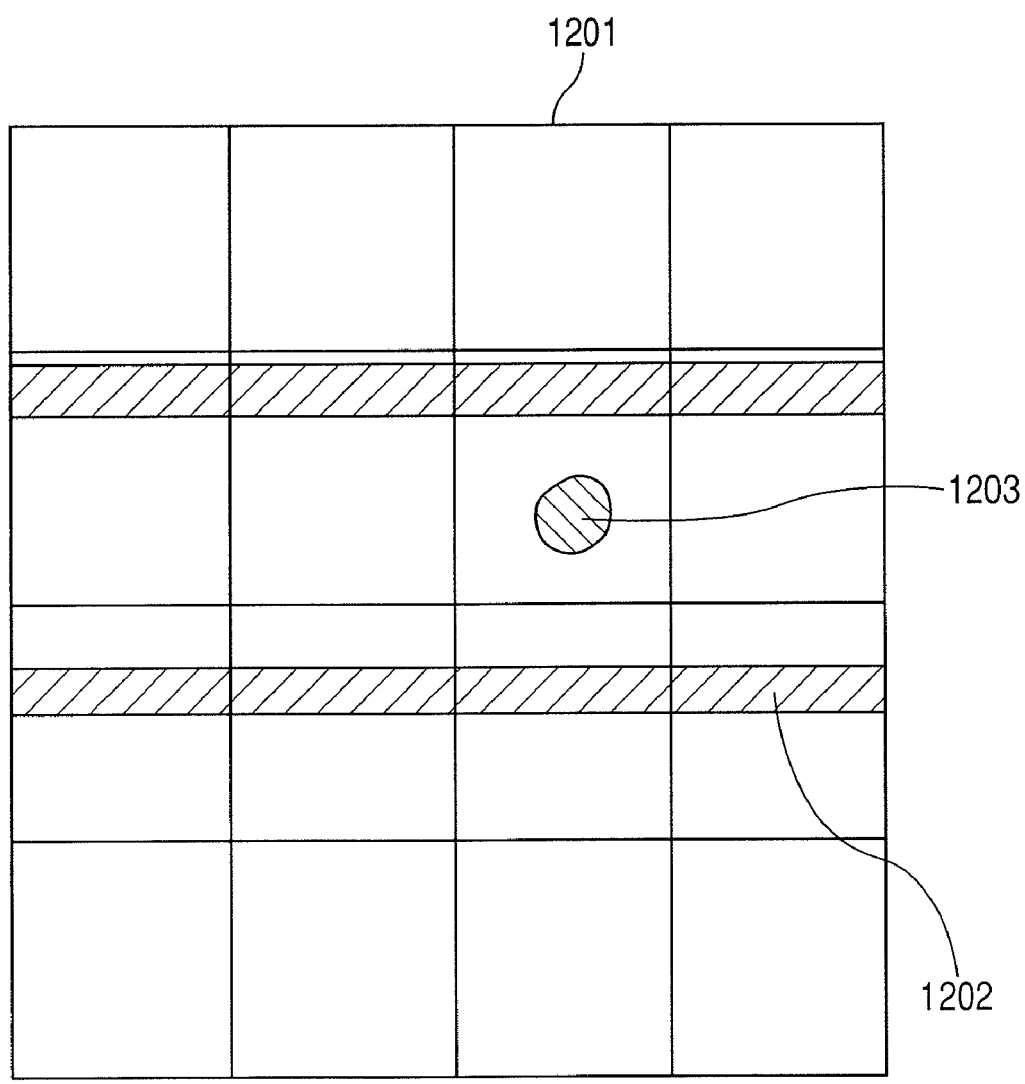
FIG. 12 is an explanatory diagram of an example of the cell comparison scheme according to the present invention.

The cell comparison scheme in the cell comparator 912 (or the like) according to the present invention features less frequent repetition of stage moving in step S30 for electron beam reference image acquisition as shown in FIG. 3B. Accordingly, two ways are likely to be usable to acquire an electron beam reference image. One is by utilizing the iterative pattern formed in any die on the semiconductor wafer, and imaging beforehand the iterative pattern one time, for example. The other is by utilizing the characteristics of the iterative pattern and combining a previously acquired electron beam defect image of the defect and an image obtained by erasing the defect from this electron beam defect image. It is also possible to utilize the iterative pattern and detect the defect by pattern matching based only on the defect image. In this case, as shown in FIG. 12, electron beam defect image 1 is split into regions of a grid format and then the regions are each matched to other regions independently (if there are wiring patterns 1202, matching is conducted between the wiring patterns). If the region matches any other split regions, the defect is regarded as having unsuccessfully been detected. When the defect image is split, if a plurality of wiring patterns are present, there is a need to split the image so that one wiring pattern exists in one split region.

In the cell comparison scheme, step S35 is executed to move the stage to the next defect position in accordance with the defect position coordinates that are output from the inspection apparatus located at a stage immediately previous to the reviewing apparatus, and then step S36 follows to acquire an electron beam defect image by electron beam imaging at that position at a first magnification. After this, step S37 is executed to detect the defect by comparing the electron beam defect image and, for example, one electron beam reference image that has been acquired beforehand. That is to say, the cell comparison scheme is subdivided into a scheme applicable only to, for example, memory cell sections having only repeating patterns, and a scheme applicable to not only memory cell sections, but also logic sections having complex wiring patterns as well as repeating patterns. Although the latter scheme (as shown in FIG. 12, the electron beam defect image 1 is split into regions of a grid format and then the regions are each matched to other regions independently) is applicable to almost all wiring patterns, except in some specific logic sections, since the latter scheme, compared with the former scheme, needs computing a great amount of data to detect the defect, the former cell comparison scheme is used for repeating patterns and the latter cell comparison scheme is used for logic sections not having repeating patterns. Throughput can be improved by so doing. However, neither of the cell comparison schemes may be effective for the defect detection. In that case, the defect detection is to use the die comparison scheme. More specifically, a defect is detected in the cell comparison scheme in step S22, then whether the next defect can be detected in the cell comparison scheme is judged in step S23, and if the next defect is judged not to be detectable in the cell comparison scheme, this comparison scheme is switched to the die comparison scheme higher in defect detection reliability, in step S24.

Figure 4:
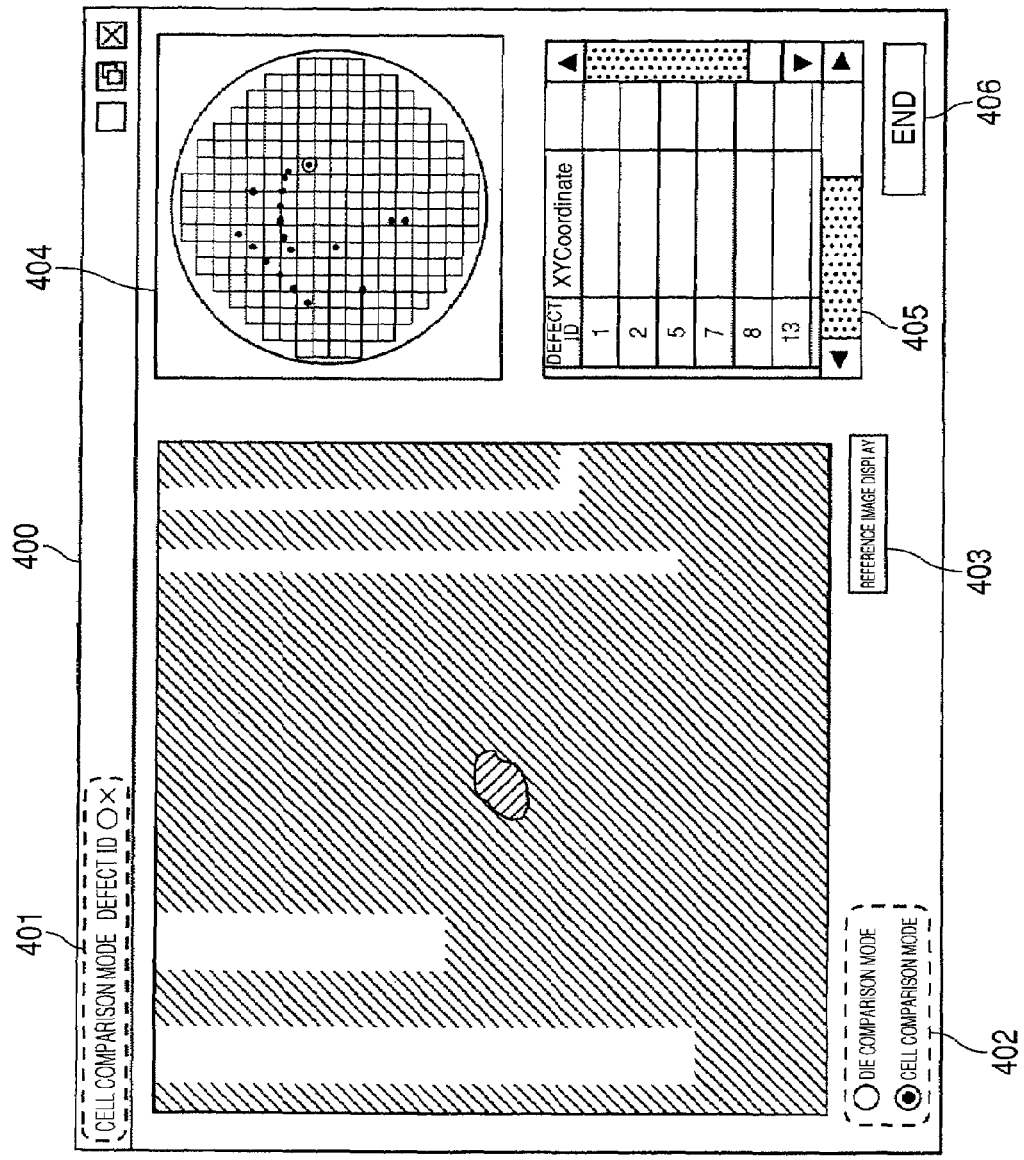
FIG. 4 is a view showing an example of graphical user interface (GUI) screen display of images obtained in the SEM-type defect-reviewing apparatus of the present invention.
Figure 5:
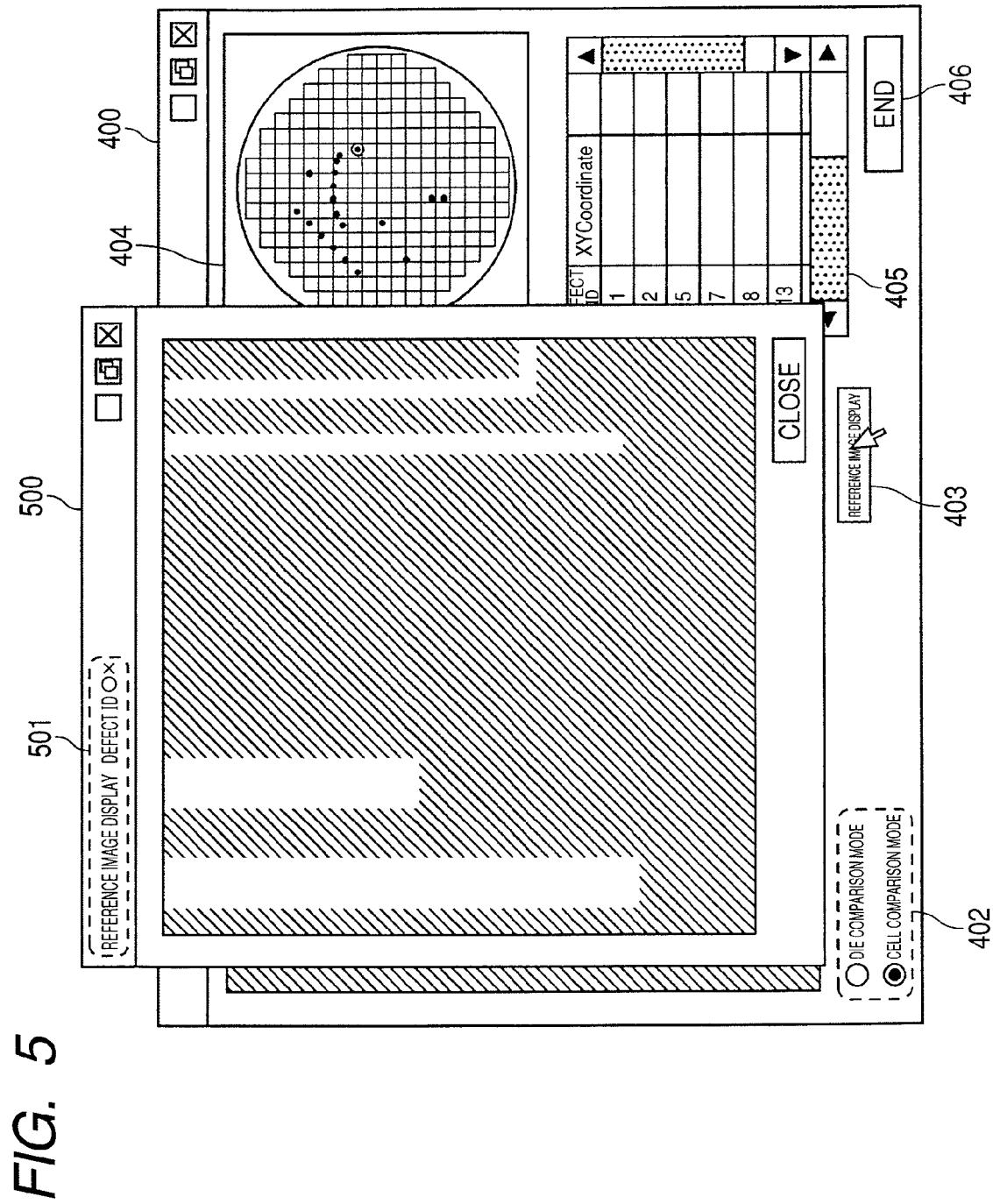
FIG. 5 is a view showing an example of GUI screen display of a reference image obtained in the SEM-type defect-reviewing apparatus of the present invention.

Next, an image display GUI menu of the display device 94 in the present first embodiment employing the defect detection with the above-described cell comparison scheme is described below using FIGS. 4 and 5. The GUI menu 400 includes a display region 401 for displaying an ID of a defect for which a review sequence is to be executed for detailed analysis of the defect, a selecting unit 402 for a user to select the review sequence to be executed, a button 403 that specifies displaying an electron beam reference image, a display region 404 for displaying a position of the defect on the semiconductor wafer, a display region 405 for displaying the ID, position, size, and other information of the defect, and a button 406 for specifying an ending process. A press of the button 403 for specifying the display of an electron beam reference image displays in a display region 501 the ID of the defect for which the electron beam reference image is to be formed. Also, the electron beam reference image is displayed in a reference image display region 500. Although the present first embodiment displays the electron beam reference image on another GUI menu 500, the reference image may be displayed on the GUI menu 400.

Next, detailed analysis of the defect by the detail analyzer 915 is described below. The present first embodiment does not use electron beam imaging at a second magnification to form an electron beam reference image. As disclosed in JP-A-2000-30652, therefore, an electron beam image of a magnification equivalent to the second magnification is first made by image processing based on an electron beam reference beam that has been formed by electron beam imaging at a first magnification. The electron beam imaging is followed by, for example, calculation of electron beam image feature values (shape, brightness, i.e., grayscale level, texture, and more) of the defect, and thus the defect is analyzed in detail. In the present first embodiment, since, even in the cell comparison scheme, using the method disclosed in JP-A-2003-98114 does not cause an electron beam reference image to be formed, even by electron beam imaging at a first magnification, the electron beam reference image needs to be made from an electron beam defect beam that has been formed by electron beam imaging at the first magnification. This is why the GUI menu 400 is required that includes the GUI display region 500 for confirming the made electron beam reference image, and the display region 402 for displaying the defect detection scheme.

Second Embodiment

In the first embodiment, the defect detection review sequence is determined from the cell comparative detection results obtained from the first several defect samples on the semiconductor wafer. In the first embodiment, however, even for a wafer with arrayed dies (chips) in which logic sections are mainly disposed, if the first several samples are selected only from memory cell sections, the defect detection in the cell comparison scheme is conducted, so the number of samples for which defect detection requires switching to the die comparison scheme due to a defect detection failure in the cell comparison scheme becomes large, which results in reduced throughput.

Figure 6:
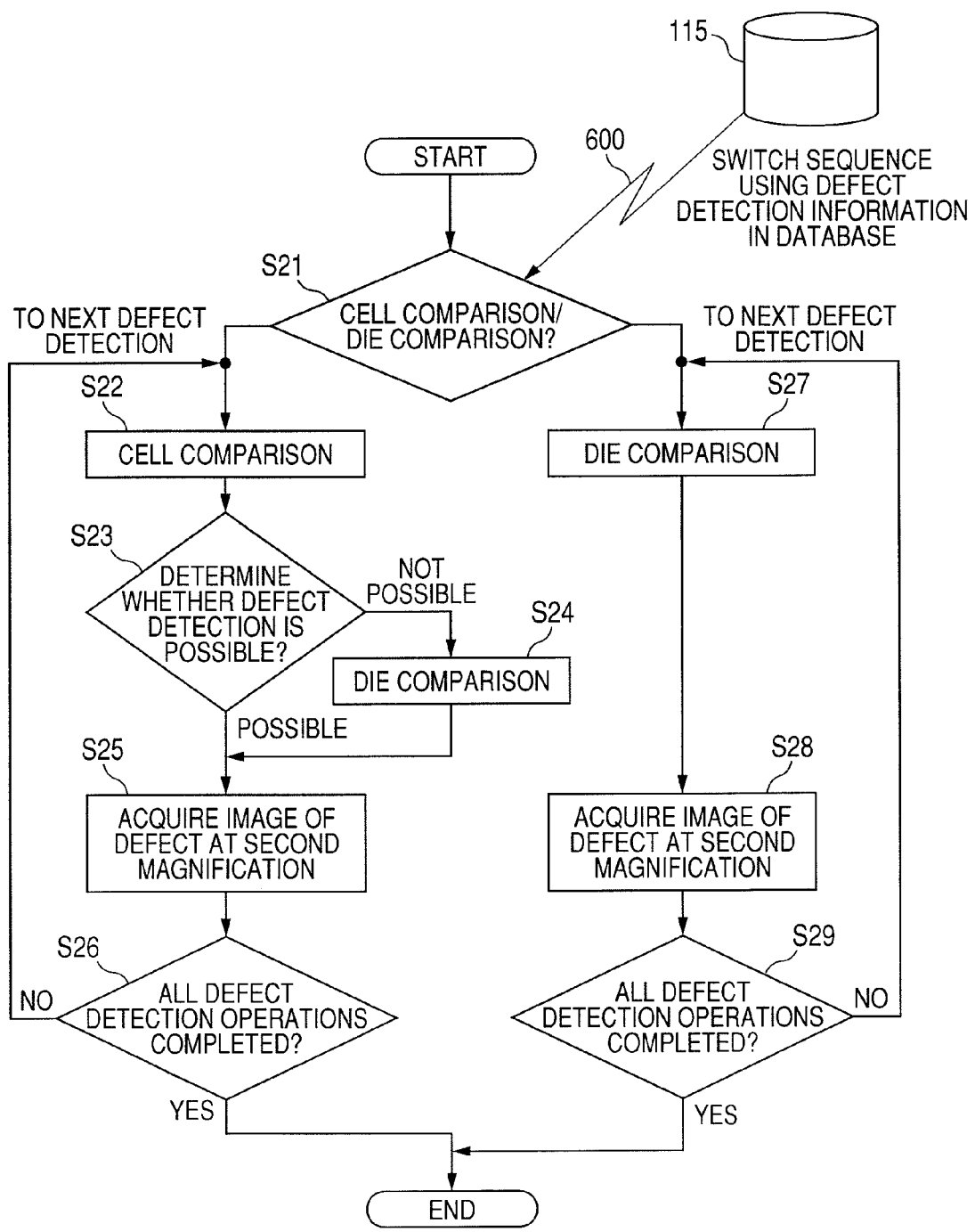
FIG. 6 is a flowchart showing a second embodiment of a review sequence adapted for detailed analysis of defects in the SEM-type defect-reviewing apparatus of the present invention.

Hence, the second embodiment of a SEM-type defect-reviewing apparatus according to the present invention differs from the first embodiment in terms of review sequence determination method. Details are described below. As shown in FIG. 6, for each semiconductor wafer (for each kind of semiconductor wafer, each process step for the semiconductor wafer), including defect detection at logic sections and defect detection at memory cell sections, the defect-reviewing apparatus 10 records in, for example, the database 115, defect detection information 600 [e.g., count of defects successfully detected in the cell comparison scheme (success ratio or success map)] that has been obtained during the past defect detection in the cell comparison scheme. For defect detection, the above-recorded information 600 [the count of defects successfully detected in the cell comparison scheme (success ratio or success map)] is retrieved from the database 115, and then in accordance with the information 600, a review sequence suitable for the semiconductor wafer to be reviewed is determined in step S21 to switch between the cell comparison scheme or die comparison scheme in the total control unit 90 or the review sequence switching unit 911 of the image processing unit 91. A reference value (threshold value) for determining the review sequence is uniquely determined by a processing time required for the die comparison scheme in step S27, and a processing time required for the cell comparison scheme in step S22 (this processing time includes the time required for switching to the die comparison scheme in the event of a defect detection failure).

In addition, in the second embodiment, even if manufacturing processes differ between semiconductor products of the same kind, since the wiring patterns formed on these semiconductor products are essentially the same, past defect detection histories obtained in the defect-reviewing apparatus 10 can be used and this provides the advantage that the review sequence can be determined from the defect detection results that the defect-reviewing apparatus obtains during defect reviews of the semiconductor wafers requiring other manufacturing processes.

Third Embodiment

A third embodiment of a SEM-type defect-reviewing apparatus according to the present invention differs from the first and second embodiments involving the selection of a review sequence (defect detection scheme) for each semiconductor wafer, in that defects are detected by selecting a defect detection scheme suitable for each defect (or each set of defects) to be reviewed. Such selection allows optimal throughput to be maintained.

Next, review sequences for performing defect detection and detailed analytical processes on semiconductor wafer surface defects, in the third embodiment of the defect-reviewing apparatus according to the present invention, are described below using FIG. 7. As with that of the first to third embodiments, a defect detection scheme in the third embodiment includes a die comparison scheme (selected in step S27) and a cell comparison scheme (selected in steps S22, S23), and one of the two schemes is appropriately selected in step S21 by the review sequence switching unit 911. The selection between the two defect detection schemes in step S21 by the review sequence switching unit 911 is performed by referring to defect detection success maps stored into the database 115, for example. In the third embodiment, the appropriate review sequence is selected, basically for each defect (or each set of defects) to be reviewed, with reference being made to the defect detection success maps compiled (summed up) for each chip on the semiconductor wafer. Therefore, if judgment result in step S23 indicates that the defect detection in the cell comparison scheme is impossible, this comparison scheme is switched to the die comparison scheme in step S27. As a result, from the defect detection possibility judgment due to the cell comparison scheme (step S23) onward, the defects to be reviewed are detected on a cell comparison basis in the coordinate system of the reviewing apparatus. Images of the thus-detected defects are acquired by electron beam imaging at a second magnification, and the defect images are stored into the image memory 916 [step 30 (S25, S28)]. From die comparison (step S27) onward, defects are detected on a die comparison basis in the coordinate system of the reviewing apparatus. Images of the thus-detected defects are acquired by electron beam imaging at a second magnification, and the defect images are stored into the image memory 916 [step 30 (S25, S28)]. This sequence is repeated until all defects on the semiconductor wafer have been detected [step 31 (S26, S29)].

The defect detection success maps are obtained through the steps described below. In the defect-reviewing apparatus 10 and the processing terminal (personal computer) 116 that can perform, for example, parallel processing, it is judged in step S33 whether or not the defect detection using the cell comparison scheme is successful, in accordance with the electron beam defect images that were stored into the database 115 after being acquired by imaging at a first magnification at each defect position on the semiconductor wafer by the defect-reviewing apparatus 10. Results of the above judgment are compiled for each chip and updated as defect detection success maps in step S34, and then the success maps are stored into the database 115, for example. Therefore, the review sequence switching unit 911 in the image processing unit 91 of the defect-reviewing apparatus 10 refers to the defect detection success maps and can thus select an appropriate defect detection scheme for the positions of each defect to be reviewed.

In order to be able to perform parallel processing with the image processing unit 91, the processing terminal (personal computer) 116 is functionally divided into a cell comparator 1161 that detects defects in the cell comparison scheme in accordance with the defect images at the defect positions on the semiconductor wafer, a judgment unit 1162 that judges whether the defect can successfully be detected by using the cell comparator, a defect detection map update unit 1163 that compiles determination results for each chip and updates compilation results as defect detection success maps, and an image memory 1164 for temporary storage of the defect images, the defect detection success maps, and the like. The processing terminal 116 further has a connected display device 1165.

Figure 8:
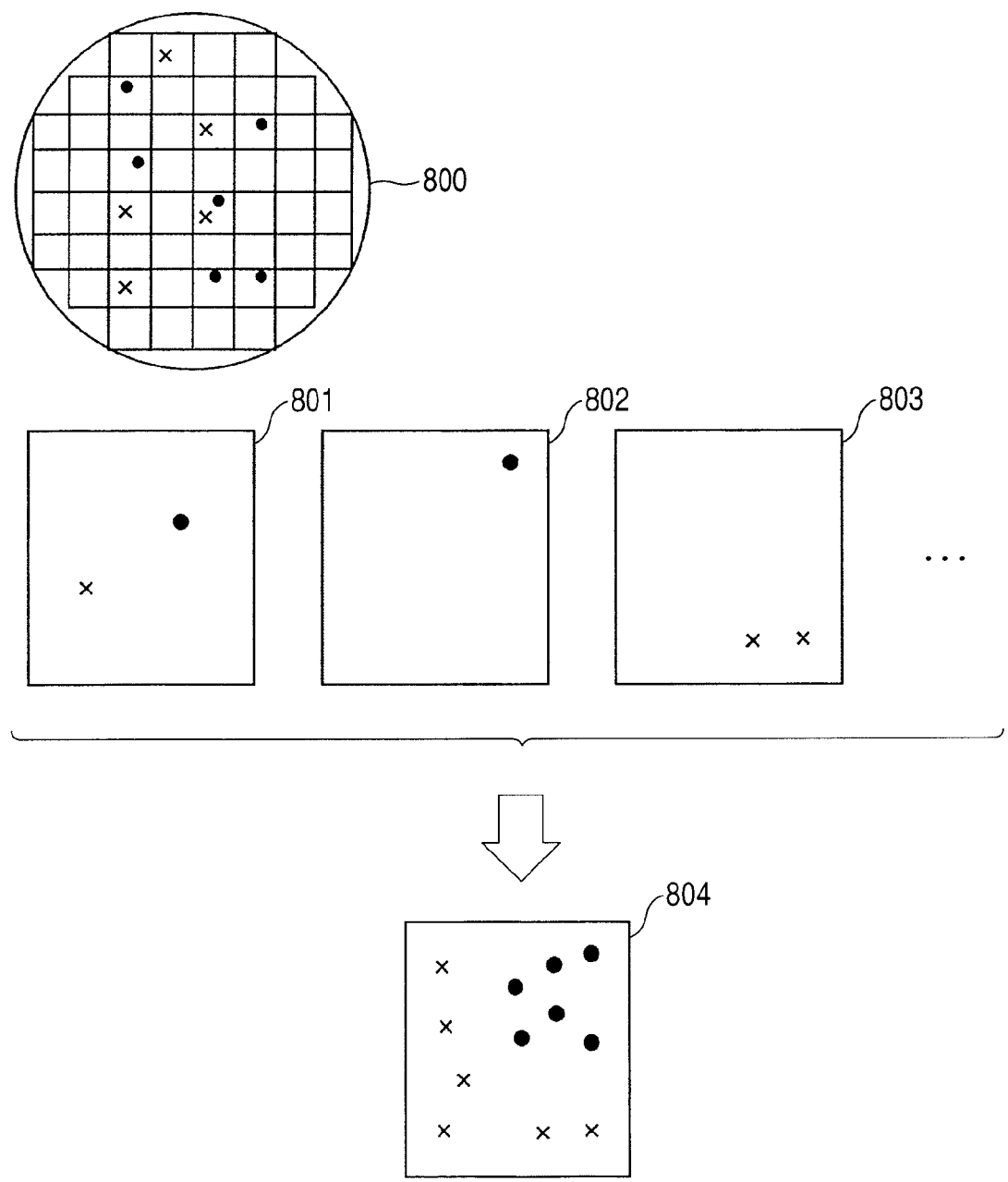
FIG. 8 is a diagram showing an example of a method in which a review sequence that was used to detect defects is recorded for creating a defect detection success map according to the present invention.
Figure 9A:
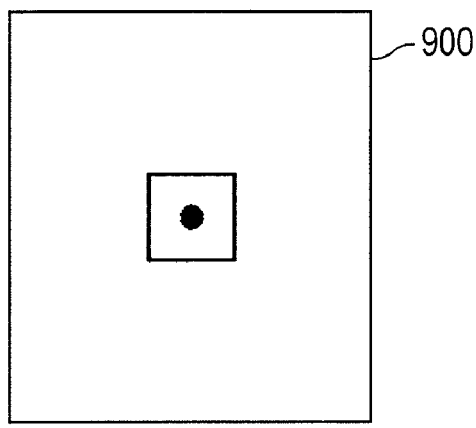
FIGS. 9A-9C show defect detection regions, FIG. 9A being a diagram showing a defect detection region specified on the GUI screen by a user, FIG. 9B being a diagram that shows defect detection executable regions set up in the cell comparison scheme and the die comparison scheme, and FIG. 9C being a diagram showing an as-integrated state of defect detection executable regions for the defects detected using the same defect detection scheme.
Figure 9B:
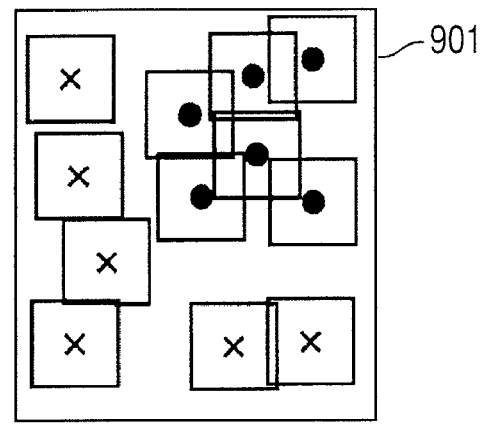
Figure 9C:
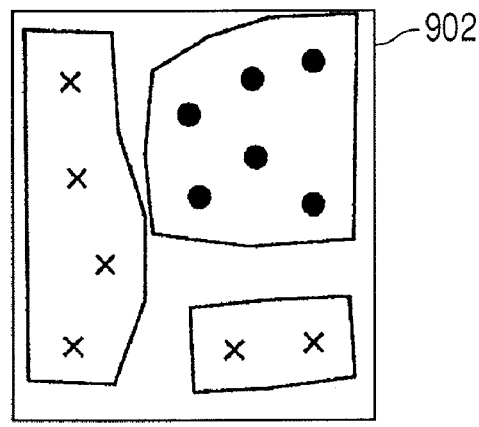
Figure 10:
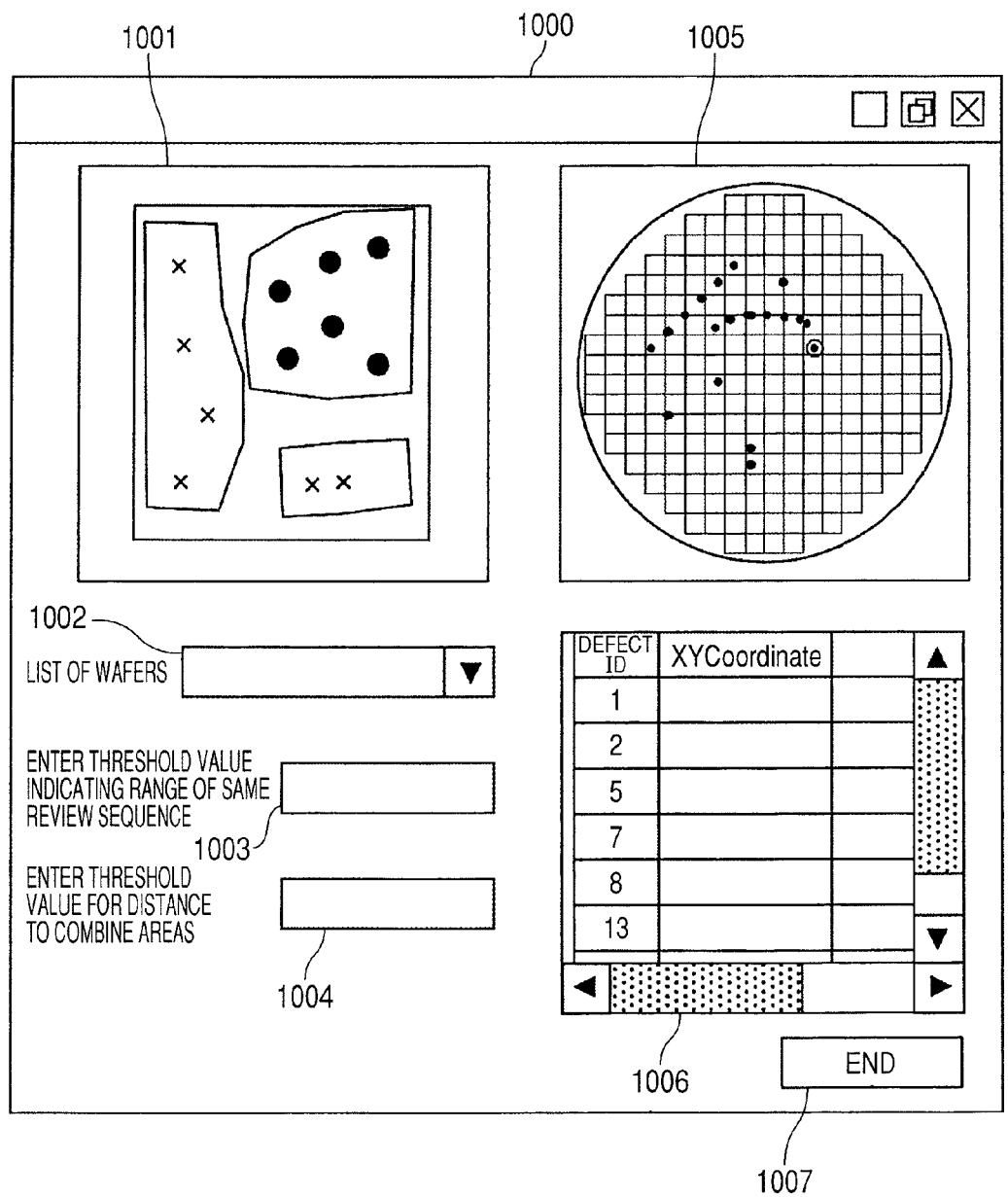
FIG. 10 is a diagram showing an example of GUI screen display for setting up defect detection success map parameters according to the present invention.

Next, a method for creation of a defect detection success map by the defect detection success map update unit 1163 of the processing terminal 116 is described below using FIGS. 8 and 9A-9C. First, the defect detection success map update unit 1163 judges whether a defect detection success map is present in the database 115. If the map is present, the defect detection success map update unit 1163 reads out the map from the database 115 and creates a new map in the procedure below. The defect detection success map update unit 1163 associates the defect detection schemes that were used to detect each defect, with defect position coordinates (801, 802, 803) obtained by converting on-wafer coordinates (800) into chip coordinates, and then records the two mutually associated kinds of information in the image memory 1164. The defect positions and the above-mentioned defect detection schemes (cell comparison scheme and die comparison scheme) are thus recorded for each chip. This state is shown in FIG. 8. Next as shown in FIG. 8, the defect detection schemes (cell comparison scheme and die comparison scheme) for each chip on the semiconductor wafer are compiled (summed up) into one chip of data (804). After this, the defect detection success map update unit 1163 uses the GUI function of the display device 1165 to select a region (in FIG. 9A, a rectangular region) present within a range specified from one of the above defect positions by a user, and set up this region as a region (900, 901) in which the defect can be detected in the particular defect detection scheme (e.g., the cell comparison scheme). FIG. 9B shows the defect detection executable region (901) set up for both the cell comparison scheme and the die comparison scheme. Next, the defect detection success map update unit 1163, by using as a reference a distance between any two defects which were detected using the same defect detection scheme, combines (integrates) the associated defect detection executable regions into one region (902) if the distance is shorter than that specified by the user. The above combination uses a polygon that surrounds all regions to be combined. At this time, if there is a region corresponding to neither the cell comparison scheme nor the die comparison scheme, this region is regarded as one for which the optimal defect detection scheme for defect detection cannot yet be determined, so this region is set up as a region in which the die comparison scheme is to be used to detect the associated defects. In this way, all regions, except those in which the cell comparison scheme is to be used to detect defects, are basically set up as the regions in which to detect defects using the die comparison scheme. There is a need, therefore, to set up the regions in which the defect detection is possible by using at least the cell comparison scheme. The defect detection success map that has thus been created is stored into the database 115. FIG. 10 shows an example of a created defect detection success map.

The defect detection success map stored within the database 115, therefore, is displayed on a GUI menu 1000 of the display device 94 of the defect-reviewing apparatus 10, and the GUI menu 1000 includes a display region 1001 to display the defect detection success map. The user uses a parameter adjusting unit to adjust a defect detection executable region (area). The user can adjust three parameters. One is contents of a wafer list 1002 listing the past defect detection histories to be used to create defect detection success maps. One is a range threshold value 1003 indicating an effective range of the defect detection scheme in which the defect detection is most likely to succeed, one is a range threshold value 1004 for combining defect detection executable regions (areas). These parameters can each be changed each time a defect is detected, and the defect detection success map is updated each time. The GUI menu 1000 may further include a display region 1005 for displaying the defect positions on the semiconductor wafer, a display region 1006 for displaying information such as defect IDs, positions, and sizes, and a button 1007 for specifying an ending process.

Next, a description is given below of a case in which neither a defect detection history of the past nor a defect detection success map is present. In this case, a defect detection success map cannot be created using the above method. Therefore, for example, the defect detection success map update unit 1163 of the processing terminal 116 creates a defect detection success map by utilizing CAD data stored within the CAD database 118, and by utilizing inspection recipes of the inspection apparatus 117 that are stored within the database 115.

First, the creation of a defect detection success map by utilizing CAD data is described. The CAD data has information of the wiring patterns formed on the semiconductor wafer, and using the CAD data allows shapes of the wafer surface in each manufacturing process to be reproduced using, for example, the processing terminal 116. The user can therefore use the processing terminal 116, for example, to reproduce all wiring patterns present on the wafer, and select either the cell or die comparison scheme as the optimal defect detection scheme, depending on whether repeating pattern exists, or by manual user setup. The defect detection success map update unit 1163 creates a defect detection success map appropriately according to the above. Each time a defect is detected, the created defect detection success map will be updated as appropriate.

Next, the creation of a defect detection success map by utilizing an inspection recipe of the inspection apparatus is described below. The inspection apparatus 117 may use CAD data and/or wiring pattern layout data to separate a desired chip region on the semiconductor wafer into cell sections and non-cell sections, and inspect each of the two kinds of sections in accordance with independent inspection parameter settings. Therefore, for example, the defect detection success map update unit 1163 of the processing terminal 116 can automatically set up cell comparative and die comparative defect detection executable regions by referring to the inspection recipe of the inspection apparatus 117. A created defect detection success map, as with that created using CAD data, will be updated each time a defect is detected.

Fourth Embodiment

In the third embodiment, only an electron beam defect image associated with the position of a defect is acquired when electron beam imaging at a second magnification higher than a first magnification is conducted to obtain the defect image for detailed analysis of the defect. A fourth embodiment of a SEM-type defect-reviewing apparatus according to the present invention, however, differs from the third embodiment in that electron beam imaging of a normal section at a second magnification is also conducted to acquire an electron beam reference image at the second magnification. In the fourth embodiment, although forming an additional electron beam image in this way requires a longer total review processing time than in the third embodiment, there is the advantage that during the detailed defect reviews using the electron beam image of the second magnification, more detailed analyses than in the third embodiment can be conducted.

Next, a semiconductor wafer surface defect detection scheme that is the fourth embodiment in the SEM-type defect-reviewing apparatus according to the present invention is described below using FIG. 11. The fourth embodiment, as with the third embodiment shown in FIG. 7, employs a defect detection scheme that includes a die comparison scheme (executed in step S27) and a cell comparison scheme (executed in steps S22, S23). A defect detection success map stored within the database 115 is referred to, whereby either of the two detection schemes is switched to the other in step S21. At this time, in the fourth embodiment, as shown in FIG. 11, an electron beam reference image obtained by imaging a normal section at a second magnification higher than a first magnification is acquired in the cell comparison scheme and die comparison scheme for detailed analyses. Stage moving (step S36) and imaging (step S37) consequently increase. Accordingly, for example, if stage moving requires 500 milliseconds and electron beam imaging requires 200 milliseconds, the total time required for processing of one defect increases to 700 milliseconds.

Meanwhile, during the detailed defect reviews using the electron beam image that was acquired at the second magnification in the detail analyzer 915 of the image processing unit 91, as disclosed in, for example, JP-A-2001-331784, a differential image between an electron beam defect image and an electron beam reference image is used to recognize surface roughness of the defect, extract wiring patterns from the electron beam reference image, and/or obtain wiring defect information from the relationship with respect to the defect position. If an electron beam reference image that was acquired at the second magnification is absent, the electron beam reference image that was acquired at the first magnification must necessarily be used to conduct the above process steps. This electron beam reference image is, in terms of resolution, inferior to the electron beam reference image that was acquired at the second magnification, the amount of information obtained will decrease. For this reason, although there are disadvantageous in comparison with the third embodiment, the fourth embodiment can provide more detailed defect information during the detailed defect analysis at a posterior stage.

The fourth embodiment can be applied to the first and second embodiments.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes that come within the meaning and range of equivalency of the claims are therefore intended to be embraced therein.

What is claimed is:

1. A method for reviewing defects of patterns in a large number of chips formed on each of semiconductor wafers, the method comprising:

a cell comparison step including of a first acquisition step of acquiring an electron beam defect image of a low magnification with moving a stage on which the wafer is mounted in accordance with position coordinate of a review defect on the wafer obtained from an inspection apparatus, and then imaging the review defect at the low magnification by using an electron beam optical system, a step of selecting a review sequence of either a cell comparison scheme or a die comparison scheme on the basis of a defect detection success ratio or defect detection success map due to at least the cell comparison scheme for each wafer or for each chip formed on the wafer, a step of, if the cell comparison scheme is selected in the sequence selection step, judging whether detection of the review defect is possible by executing the selected cell comparison scheme based on the electron beam defect image acquired from the review defect at the low magnification in the first acquisition step, and a first calculation step of, if judgment result in the detection possibility judgment step indicates that the detection of the review defect is possible, calculating position coordinate of the detected review defect in a coordinate system of a defect-reviewing apparatus;

a die comparison step including of a second acquisition step of, if the judgment result in the detection possibility judgment step indicates that the detection of the review defect is impossible, or if the die comparison scheme is selected in the sequence selection step, acquiring an electron beam reference image at a low magnification for a normal part to perform the selected die comparison scheme by using the electron beam optical system with moving the stage, and a second calculation step of detecting the review defect by performing the selected die comparison scheme between the electron beam defect image of the review defect at the low magnification acquired in the first acquisition step and the electron beam reference image of the low magnification acquired in the second acquisition step, and calculating the position coordinate of the detected review defect in the coordinate system of the defect-reviewing apparatus; and a defect image acquisition step of acquiring electron beam defect images of a high magnification by imaging the review defects at the high magnification by using the electron beam optical system in accordance with the position coordinates of the review defects calculated in the coordinate system of the defect-reviewing apparatus in the first and second calculation steps.

2. The method for reviewing defects of patterns according to claim 1, wherein, in the selection step, the selection of either the cell comparison scheme or the die comparison scheme is performed for each wafer or for each defect that is to be reviewed.

3. The method for reviewing defects of patterns according to claim 1, wherein the cell comparison uses a previously provided electron beam reference image of a low magnification or an electron beam reference image made at a low magnification based on the electron beam defect image imaged the review defect at the low magnification.

4. A method for reviewing defects of patterns in a large number of chips formed on each of semiconductor wafers, the method comprising:

a cell comparison step including of a first acquisition step of acquiring an electron beam defect image of a low magnification by moving a stage on which the wafer is mounted in accordance with position coordinate of a review defect on the wafer obtained from an inspection apparatus, and then imaging the review defect at the low magnification by using an electron beam optical system, a step of previously providing a defect detection success ratio or defect detection success map due to at least the cell comparison scheme for each wafer or for each chip formed on the wafer, a step of selecting a review sequence of either the cell comparison scheme or a die comparison scheme on the basis of the defect detection success ratio or defect detection success map due to at least the cell comparison scheme for each wafer or for each chip formed on the wafer previously provided in the provision step, a step of, if the cell comparison scheme is selected in the sequence selection step, judging whether detection of the review defect is possible by executing the cell comparison scheme based on the electron beam defect image acquired from the review defect at the low magnification in the acquisition step, and a first calculation step of, if judgment result in the detection possibility judgment step indicates that the detection of the review defect is possible, calculating position coordinate of the detected review defect in a coordinate system of a defect-reviewing apparatus;

a die comparison step including of a second acquisition step of, if the judgment result in the detection possibility judgment step indicates that the detection of the review defect is impossible, or if the die comparison scheme is selected in the sequence selection step, acquiring an electron beam reference image at a low magnification for a normal part to perform the die comparison scheme by using the electron beam optical system with moving the stage, and a second calculation step of detecting the review defect by performing the die comparison scheme between the electron beam defect image of the review defect at the low magnification acquired in the first acquisition step and the electron beam reference image of the low magnification acquired in the second acquisition step, and calculating the position coordinate of the detected review defect in the coordinate system of the defect-reviewing apparatus; and a defect image acquisition step of acquiring an electron beam defect images of a high magnification by imaging the review defects at the high magnification by using the electron beam optical system in accordance with the defect position coordinates calculated in the coordinate system of the defect-reviewing apparatus in the first and second calculation steps.

5. The method for reviewing defects of patterns according to claim 4, wherein, in the provision step, the defect detection success ratio or defect detection success map due to at least the cell comparison scheme for each wafer or for each chip formed on the wafer, is calculated by performing the cell comparison scheme based on an electron beam defect image of the low magnification acquired from a sample of a review defect by using the sample of the review defect present on the wafer mounted on the stage.

6. The method for reviewing defects of patterns according to claim 5, wherein, in the provision step, the calculated defect detection success ratio or defect detection success map due to at least the cell comparisons scheme is displayed on a GUI unit.

7. The method for reviewing defects of patterns according to claim 4, wherein, in the provision step, the defect detection success ratio or defect detection success map due to at least the cell comparisons scheme for each wafer or each chip, is calculated based on historical information due to the cell comparison scheme for a wafer of the same kind as that of the wafer mounted on the stage.

8. The method for reviewing defects of patterns according to claim 4, wherein, in the provision step, whether the defect detection due to the cell comparison succeeds or fails is judged based on the electron beam defect image of the low magnification, acquired at the review defect position, and the defect detection success map due to at least the cell comparison scheme for each chip is calculated by summing up the judgment result for the each chip.

9. The method for reviewing defects of patterns according to claim 8, wherein, when the calculation of the defect detection success map due to at least the cell comparison scheme for the each chip, is calculated, regions in which the defect detection due to the cell comparison scheme is possible are integrated on the basis of a distance between the review defects for which the defect detection has been performed by using the cell comparison scheme.

10. The method for reviewing defects of patterns according to claim 4, wherein, in the selection step, the selection of either the cell comparison scheme or the die comparison scheme is performed for each wafer or for each defect that is to be reviewed.

11. The method for reviewing defects of patterns according to claim 4, wherein the cell comparison scheme uses a previously provided electron beam reference image of a low magnification or an electron beam reference image of a low magnification made based on the electron beam defect image imaged the review defect at the low magnification.

12. A SEM-type defect-reviewing apparatus, comprising:
a cell comparator including of
    a first acquisition unit which acquires an electron beam defect image of a low magnification with moving a stage on which a wafer is mounted in accordance with position coordinate of a review defect on the wafer obtained from an inspection apparatus, and then images the review defect at the low magnification by using an electron beam optical system,
    a review sequence selector which selects a review sequence of either a cell comparison scheme or a die comparison scheme on the basis of a defect detection success ratio or defect detection success map due to at least the cell comparison scheme for each wafer or for each chip formed on the wafer,
    a detection possibility judgment unit which, if the cell comparison scheme is selected in the review sequence selector, judges whether detection of the review defect is possible by executing the selected cell comparison scheme based on the electron beam defect image acquired from the review defect at the low magnification in the first acquisition unit, and
    a first calculator which, if judgment result in the detection possibility judgment unit indicates that the detection of the review defect is possible, calculates position coordinate of the detected review defect in a coordinate system of a defect-reviewing apparatus;
a die comparator including of
    a second acquisition unit which, if the judgment result in the detection possibility judgment unit indicates that the detection of the review defect is impossible, or if the die comparison scheme is selected in the review sequence selector, acquires an electron beam reference image at a low magnification for a normal part to perform the selected die comparison scheme by using the electron beam optical system with moving the stage, and
    a second calculator which detects the review defect by performing the selected die comparison scheme between the electron beam defect image of the review defect at the low magnification acquired in the first acquisition unit and the electron beam reference image of the low magnification acquired in the second acquisition unit, and calculates the position coordinate of the detected review defect in the coordinate system of the defect-reviewing apparatus; and
a high-magnification defect image acquisition unit which acquires electron beam defect images of a high magnification by imaging the review defects at the high magnification by using the electron beam optical system in accordance with the position coordinates of the review defects calculated in the coordinate system of the defect-reviewing apparatus in the first and second calculators.

13. The SEM-type defect-reviewing apparatus according to claim 12, further comprising a detail analyzer which calculates at least feature quantities of electron beam image by performing detailed analyses with using the electron beam defect image of the high magnification acquired from the defect image acquisition unit.

14. The SEM-type defect-reviewing apparatus according to claim 12, further comprising a provision unit which comprises so as to calculate the defect detection success ratio or defect detection success map due to at least the cell comparison scheme for each wafer or for each chip formed on the wafer by performing the cell comparison scheme based on an electron beam defect image of the low magnification acquired from a sample of a review defect by using the sample of the review defect present on the wafer mounted on the stage.

15. The SEM-type defect-reviewing apparatus according to claim 12, wherein in the selector, the selection of either the cell comparison scheme or the die comparison scheme is performed for each wafer or for each defect that is to be reviewed.

16. A SEM-type defect-reviewing apparatus, comprising:
a cell comparator including of
    a first acquisition unit which acquires an electron beam defect image of a low magnification with moving a stage on which a wafer is mounted in accordance with position coordinate of a review defect on the wafer obtained from an inspection apparatus, and then images the review defect at the low magnification by using an electron beam optical system,
    a provision unit which previously provides a defect detection success ratio or defect detection success map due to at least the cell comparison scheme for each wafer or for each chip formed on the wafer,
    a review sequence selector which selects a review sequence of either the cell comparison scheme or a die comparison scheme on the basis of the defect detection success ratio or defect detection success map due to at least the cell comparison scheme for each wafer or for each chip previously provided in the provision unit,
    a detection possibility judgment unit which, if the cell comparison scheme is selected in the review sequence selector, judges whether detection of the review defect is possible by executing the cell comparison scheme based on the electron beam defect image acquired from the review defect at the low magnification, and
    a first calculator which, if judgment result in the detection possibility judgment unit indicates that the detection of the review defect is possible, calculates position coordinate of the detected review defect in a coordinate system of a defect-reviewing apparatus;
a die comparator including of
    a second acquisition unit which, if the judgment result in the detection possibility judgment unit indicates that the detection of the review defect is impossible, or if the die comparison scheme is selected in the review sequence selector, acquires an electron beam reference image at a low magnification for a normal part to perform the die comparison scheme by using the electron beam optical system with moving the stage, and
    a second calculator which detects the review defect by performing the die comparison scheme between the electron beam defect image of the defect at the low magnification acquired in the first acquisition unit and the electron beam reference image of the low magnification acquired in the second acquisition unit, and calculates the position coordinate of the detected review defect in the coordinate system of the defect-reviewing apparatus; and
a defect image acquisition unit which acquires an electron beam defect image of a high magnification by imaging the review defects at the high magnification by using the electron beam optical system in accordance with the defect position coordinates calculated in the coordinate system of the defect-reviewing apparatus in the first and second calculators.

17. The SEM-type defect-reviewing apparatus according to claim 16, further comprising a detail analyzer which calculates at least feature quantities of electron beam image by performing detailed analyses with using the electron beam defect image of the high magnification acquired from the defect image acquisition unit.

18. The SEM-type defect-reviewing apparatus according to claim 16, wherein the provision unit section comprises so as to calculate the defect detection success ratio or defect detection success map due to at least the cell comparison scheme for each wafer or for each chip formed on the wafer by performing the cell comparison scheme based on an electron beam defect image of the low magnification acquired from a sample of a review defect by using the sample of the review defect present on the wafer mounted on the stage.

19. The SEM-type defect-reviewing apparatus according to claim 16, wherein the provision unit comprises so as to calculate the defect detection success ratio or defect detection success map due to at least the cell comparisons scheme for each wafer or each chip, based on historical information due to the cell comparison scheme for a wafer of the same kind as that of the wafer mounted on the stage.

20. The SEM-type defect-reviewing apparatus according to claim 16, wherein the provision unit comprises so that whether the defect detection due to the cell comparison succeeds or fails is judged based on the electron beam defect image of the low magnification, acquired at the review defect position, and the defect detection success map due to at least the cell comparison scheme for each chip is calculated by summing up the judgment result for the each chip.

21. The SEM-type defect-reviewing apparatus according to claim 16, further comprising a GUI unit; wherein, after being calculated in the provision unit, the defect detection success ratio or defect detection success map due to at least the cell comparison scheme is displayed on the GUI unit.

* * * * *